United States Patent [19]

Kariyone et al.

[11] 4,016,205

[45] Apr. 5, 1977

[54] PROCESS FOR THE OPTICAL RESOLUTION OF DL-2-(4-HYDROXYPHENYL)GLYCINE

[75] Inventors: Kazuo Kariyone, Kyoto; Hideo Yagi, Toyonaka; Kazuhiko Yoshida, Hirakata, all of Japan

[73] Assignee: Fujisawa Pharmaceutical Co., Ltd., Osaka, Japan

[22] Filed: Sept. 12, 1975

[21] Appl. No.: 612,660

[30] Foreign Application Priority Data

Sept. 12, 1974  Japan ............................ 49-105805

[52] U.S. Cl. .......................... 260/519; 260/501.19; 260/503
[51] Int. Cl.² .................................... C07C 101/30
[58] Field of Search ............. 260/519, 501.19, 503

[56] References Cited

UNITED STATES PATENTS

| | | | |
|---|---|---|---|
| 3,381,031 | 4/1968 | Dwyer et al. | 260/519 |
| 3,832,388 | 8/1974 | Lorenz | 260/519 |
| 3,890,379 | 6/1975 | Schawartz | 260/519 |

*Primary Examiner*—Norman Morgenstern
*Attorney, Agent, or Firm*—Bierman & Bierman

[57] ABSTRACT

This invention relates to a process of resolving D and L-2-(4-hydroxyphenyl) glycine. DL-2-(4-hydroxyphenyl) glycine is treated with d-3-bromo-2-oxo-10-bornanesulfonic acid to form a mixture of d-3-bromo-2-oxo-10-bornanesulfonic acid salts of D- and L-2-(4-Hydroxyphenyl) glycine. This mixture is treated with a solvent selected from the group consisting of isobutyl alcohol, a mixture of a lower alkanol and chloroform, or a mixture of a lower alkanol and toluene. The precipitate containing the d-3-bromo-2-oxo-10 bornanesulfonic acid salt of L-2-(4-hydroxyphenyl) glycine is collected. The corresponding acid salt of D-2-(hydroxyphenyl) glycine is collected from the mother liquor. D- and L-2-(4-hydroxyphenyl) glycine are then recovered by conventional means.

24 Claims, No Drawings

PROCESS FOR THE OPTICAL RESOLUTION OF DL-2-(4-HYDROXYPHENYL)GLYCINE

The present invention relates to a new process for the resolution of DL-2-(4-hydroxyphenyl)glycine. More particularly, the present invention relates to a new process for the isolation of D- and L-2-(4-hydroxyphenyl)glycine from DL-2-(4-hydroxyphenyl)-glycine by a chemical resolution.

With regard to a process for the resolution of D-2-(4-hydroxyphenyl)glycine from DL-2-(4-hydroxyphenyl)glycine various methods have been known and disclosed in the literature as listed below in chemical methods (I) and enzymatic methods (II).

(I) Chemical methods (1) German Offenlegungsschrift 2, 345, 302

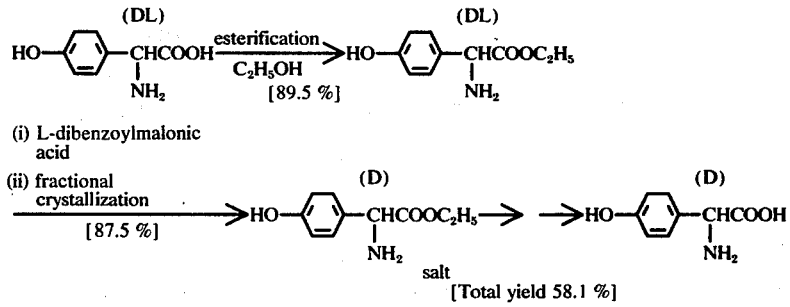

(2) U.S.P. 3, 796, 748

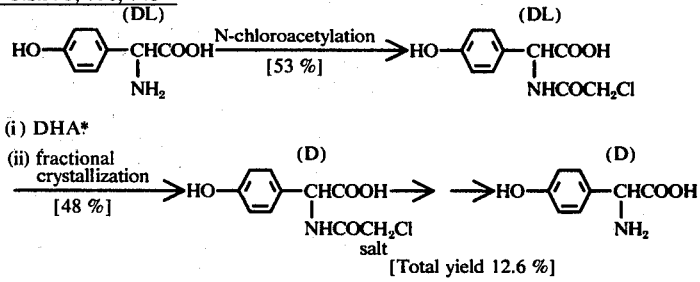

(3) Belgian Patent 772, 894

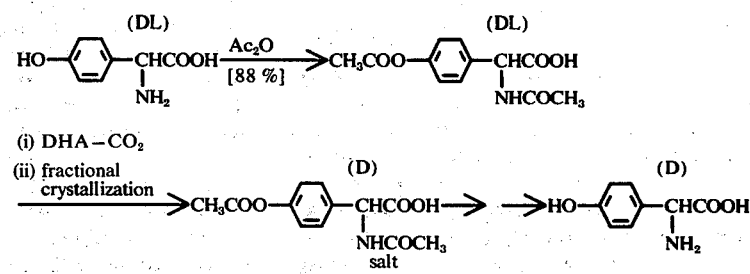

(4) British Patent 1, 314, 739

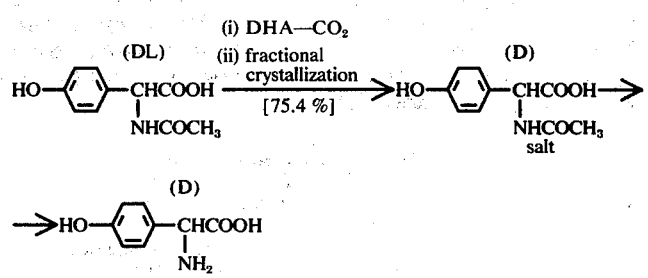

(5) U.S.P. 3, 705, 900

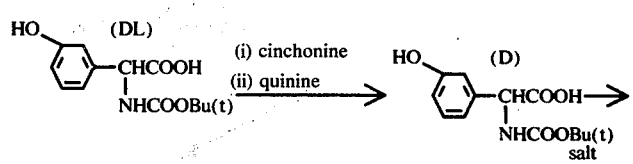

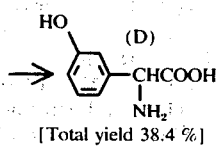
[Total yield 38.4 %]

(II) Enzymatic methods (I) U.S.P. 3, 517, 023

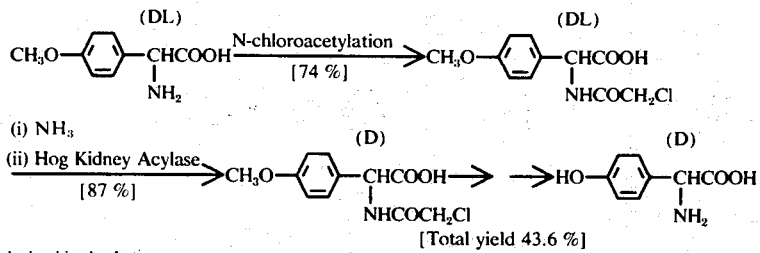

*DHA: dehydroabietylamine

These known methods have the following defects.
(i) In the process, it is necessary to protect temporarily at least one of the hydroxy, amino and carboxy groups in the DL-2-(4-hydroxyphenyl)glycine before the resolution.
(ii) In the last step, it is necessary to eliminate the protecting group to provide D-2-(4-hydroxyphenyl)glycine.
(iii) When DL-2(4-hydroxyphenyl)glycine is used as the starting material, the known methods require 4 or 5 steps to provide D-2-(4-hydroxyphenyl)glycine.
(iv) Total yields of D-2-(4-hydroxyphenyl)glycine from DL-2-(4-hydroxyphenyl)glycine are low due to the requirements as stated in the above (i), (ii) (iii).

In the course of study for the resolution of D-2-(4-hydroxyphenyl)glycine by chemical resolution of its racemate, the present inventors have found out that d-3-bromo-2-oxo-10-bornanesulfonic acid salt of L-2-(4-hydroxyphenyl)glycine forms selectively a solvate with isobutyl alcohol, chloroform or toluene, which is insoluble in those solvents or a mixture thereof and can be easily separated out from another enantiomer, which does not form any solvate and is soluble in those solvents or a mixture thereof. These findings encouraged the present inventors to make further successive study so that the present inventors have been able to provide an newly improved process for the isolation of D- and L-2-(4-hydroxyphenyl)glycine from the racemate. That is, the process of the present invention has been advantageously improved in the following manner:
(i) under the conditions of the present invention, any temporary protection of the hydroxy, amino and/or carboxy group(s) in the DL-2-(4-hydroxyphenyl)glycine is unnecessary,
(ii) it is unnecessary to eliminate the said protecting group(s) in the last steps,
(iii) the number of steps necessary to obtain D-2-(4-hyroxyphenyl) glycine from DL-2-(4-hydroxyphenyl) glycine are reduced, and
(iv) the yield of the D-2-(4-hydroxyphenyl)glycine from DL-2-(4-hydroxyphenyl)glycine can be much higher than those of the known methods.

D-2-(4-hyroxyphenyl)glycine is used as an important starting material for introducing the side-chain at 6- or 7-amino group in semi-synthetic penicillins or cephalosporins.

The process of the present invention comprises treating DL-2-(4-hydroxyphenyl)glycine with d-3-bromo-2-oxo-10-bornane-sulfonic acid to form a mixture of d-3-bromo-2-oxo-10-bronanesulfonic acid salts of D- and L-2-(4-hydroxyphenyl)glycine, treating the mixture with isobutyl alcohol or a mixture of lower alkanol and chloroform or toluene to selectively precipitate a solvate of the d-3-bromo-2-oxo-10-bornanesulfonic acid salt of L-2-(4-hydroxyphenyl)-glycine with isobutyl alcohol, chloroform or toluene, collecting the precipitates, obtaining d-3-bromo-2-oxo-10-bornanesulfonic acid salt of D-2-(4-hydroxyphenyl)glycine from the mother liquor and then recovering pure, crystalline D-2-(4-hydroxyphenyl) glycine from said salt and L-2-(4-hydroxyphenyl) glycine from said solvate.

For reference, the process of the present invention is shown by the following diagram.

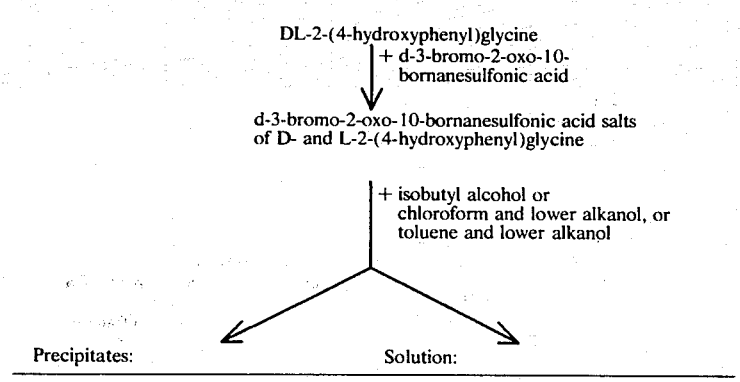

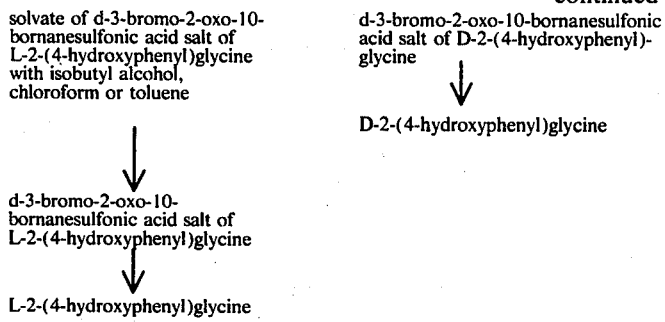

The process of the present invention may be carried out, at first, by treating a racemic mixture of D- and L-2-(4-hydroxyphenyl)glycine with d-3-bromo-2-oxo-10-bornanesulfonic acid, preferably in a solvent such as lower alkanol (e.g. methanol, ethanol, propanol, isopropyl alcohol, butanol, isobutyl alcohol, t-butyl alcohol, etc.), in which d-3-bromo-2-oxo-10-bornanesulfonic acid may be preferably used in a theoretical or slight excess amount of the starting DL-2-(4-hydroxyphenyl)glycine. The reaction temperature is not restrictive, but it may be preferably carried out at an ambient temperature or under heating. In this step, when any insoluble substances are produced in the reaction mixture, it is desirable to remove said insoluble substances from the reaction mixture before the successive treatment is conducted.

As the second step, a mixture of d-3-bromo-2-oxo-10-bornanesulfonic acid salts of D- and L-2-(4-hydroxyphenyl)glycine thus produced is treated with a solvent selected from isobutyl alcohol, a mixture of chloroform and lower alkanol or a mixture of toluene and lower alkanol. As a suitable example of lower alkanol, there may be used the same lower alkanol as illustrated in the previous step. The ratio of chloroform or toluene and lower alkanol may vary depending upon the lower alkanol used. Generally, the ratio of chloroform or toluene to the mixed solvent is higher than that of lower alkanol to the mixed solvent.

The ratio of chloroform or toluene to solvate used in the present invention varies depending upon the polarity of the particular alkanol employed. The lower the polarity of the lower alkanol, the lower the ratio of chloroform or toluene to solvate. The greater the polarity of the lower alkanol, the higher the ratio of chloroform or toluene to solvate.

In the second step, isobutyl alcohol may be used alone or may be used in an admixture with the other lower alkanol. Further, in case that lower alkanol is used as a solvent in the previous first step, the second step may be also conducted by treating the reaction mixture comprising said salts of D- and L-2-(4-hydroxyphenyl)glycine with chloroform or toluene only. Additionally, when the previous first step is conducted in isobutyl alcohol as the solvent, the solvate of the d-3-bromo-2-oxo-10-bornanesulfonic acid salt of L-2-(4-hydroxyphenyl)glycine with isobutyl alcohol may precipitate directly in the reaction mixture so that this second step may be omitted. According to the treatment of the second step as explained above, d-3-bromo-2-oxo-10-bornanesulfonic acid salt of L-2-(4-hydroxyphenyl)glycine selectively precipitates in the mixture as the solvate with isobutyl alcohol, chloroform or toluene, while d-3-bromo-2-oxo-10-bronanesulfonic acid salt of D-2-(4-hydroxyphenyl)glycine remains in the solution.

As the third step, the solvate of d-3-bromo-2-oxo-10-bornanesulfonic acid salt of L-2-(4-hydroxyphenyl)glycine with isobutyl alcohol, chloroform or toluene is isolated from the mixture obtained in the previous second step by a conventional method such as filtration, centrifugation, etc. Accordingly, d-3-bromo-2-oxo-10-bornanesulfonic acid salt of D-2-(4-hydroxyphenyl)glycine remains in the mother liquor. This remaining salt can be obtained from the said mother liquor in a conventional manner such as evaporation, etc. and, when desired, purified in a conventional manner. D-2-(4-hydroxyphenyl)glycine can be recovered from the thus obtained d-3-bromo-2-oxo-10-bornanesulfonic acid salt of D-2-(4-hydroxyphenyl)glycine by a conventional method, for example, by dissolving the salt into a suitable polar solvent or a mixture thereof, treating the solution with a base showing stronger basicity than that of 2-(4-hydroxyphenyl)glycine and then acidifying the resultant solution to around pH 5 with a conventional acid to precipitate D-2-(4-hydroxyphenyl)glycine, which is collected and purified by a conventional manner. In said resolution process, as a suitable polar solvent, there may be used a lower alkanol such as methanol, ethanol, or the like. As a base, there may be used ammonium hydroxide, or the like and as an acid there may be used acetic acid, or the like.

In addition, L-2-(4-hydroxyphenyl)glycine can be recovered from thus obtained solvate of d-3-bromo-2-oxo-10-bornanesulfonic acid salt of L-2-(4-hyroxyphenyl)glycine with isobutyl alcohol, chloroform or toluene in a similar manner to the above.

The invention is illustrated by the following Examples:

EXAMPLE 1

(1) A mixture of DL-2-(4-hydroxyphenyl)glycine (20 g.), d-3-bromo-2-oxo-10-bornanesulfonic acid (39.2 g.) and isopropyl alcohol (150 ml.) was stirred at 60° C for 30 minutes. After removing insoluble substances from the reaction mixture, the filtrate was concentrated under reduced pressure to make the amount of isopropyl alcohol equal to 120 g. 370 g. of toluene was added to the mixture which was then seeded with a small amount (10 mg.) of d-3-bromo-2-oxo-10-bornane-sulfonic acid salt of L-2-(4-hydroxyphenyl)glycine. This acid salt was previously prepared in a manner similar to the above and crystallized from a similar mixture except for the presence of a greater amount of toluene and crystallizing from the similar mixture but containing further increased amount of toluene than that of the above. The mixture was stirred at 15° C for 3.5 hours. The precipitating crystals were collected by filtration, washed with a mixture (50 ml.) of toluene and isopropyl alcohol (4 : 1), and dried at room temperature for 12 hours under reduced pressure (5 mmHg) to give the solvate (30 g.) of d-3-bromo-2-oxo-10-bornanesulfonic acid salt of L-2-(4-hydroxyphenyl)glycine with toluene, m.p. 196 to 197° C (decomp.).

$[\alpha]_D^{20} + 109°$ (C = 1, H$_2$O)

A solution of the solvate (30 g.) obtained above and hot methanol (60 ml.) was evaporated to dryness under reduced pressure. After dissolving the oily residue in isopropyl alcohol (50 g.), toluene (200 g.) was added to the solution and the solution was treated similarly to the above to give the pure solvate (29 g.), m.p. 199° C (decomp.). Differential thermal analaysis of the solvate gave the endothermic peak at 150° C.

$[\alpha]_D^{20} + 120°$ (C=1, H$_2$O)

Toluene was released from the solvent by drying at 70° C for 24 hours under reduced pressure (1 mmHg) to give d-3-bromo-2-oxo-10-bornanesulfonic acid salt of L-2-(4-hydroxyphenyl)glycine.

$[\alpha]_D^{20} + 131°$ (C=1, H$_2$O)

The solvate (29 g.) of the d-3-bromo-2-oxo-10-bornanesulfonic acid salt of L-2-(4-hyroxyphenyl)glycine with toluene was dissolved in 90% methanol (75 ml.) and the solution was adjusted to pH 7 with 28% ammonium hydroxide and then to pH 5 with acetic acid. The solution was stirred under warming until precipitates were formed, and then methanol (2 times the volume of the solution) was added, and allowed to stand overnight under cooling. The precipitates were collected by filtration, washed with methanol and dried to give crystals of L-2-(4-hydroxyphenyl)glycine (8.4 g.), m.p. 214° to 215° C (decomp.).

$[\alpha]_D^{20} + 108°$ (C=1, H$_2$O)

(2) The filtrate and the washings, which were obtained in the above by removing the crude solvate of d-3-bromo-2-oxo-10-bornanesulfonic acid salt of L-2-(4-hydroxyphenyl)glycine with toluene, were evaporated under reduced pressure and the oily residue was dissolved in isopropyl alcohol (50 ml.). The solution was concentrated again under reduced pressure. Isopropyl alcohol was added to the oily residue such that the amount of isopropyl alcohol was equal to 37g After adding toluene (130 g.), the solution was seeded with the authenic specimen of d-3-bromo-2-oxo-10-bornane-sulfonic acid salt of D-2-(4-hydroxyphenyl)glycine which was prepared preliminarily by a conventional manner, and then stirred for 4 hours at 30° C. The precipitating crystals were collected by filtration, washed with a mixture of toluene and isopropyl alcohol (4 : 1), and dried to give d-3-bromo-2-oxo-10-bornanesulfonic acid salt of D-2-(4-hydroxyphenyl)glycine (27.0 g.), m.p. 208 to 209° C (decomp.).

$[\alpha]_D^{20} + 11.8°$ (C=1, H$_2$O)

A solution of the salt (27 g.) obtained above in hot methanol (50 ml.) was evaporated under reduced pressure. The oily residue were dissolved in isopropyl alcohol (50 ml.) and evaporated under reduced pressure. The oily reduced was dissolved again in isopropyl alcohol (30 g.) 130 g. of toluene were added to the solution. Then the solution was seeded with the authenic specimen of d-3-bromo-2-oxo-10-bornanesulfonic acid salt of D-2-(4-hydroxyphenyl)-glycine and stirred for 3 hours at 30° C. The precipitating crystals were collected by filtration, washed with a mixture of toluene and isopropyl alcohol (4 : 1) and then dried to give the pure d-3-bromo-2-oxo-10-bornanesulfonic acid salt of D-2-(4-hydroxyphenyl)glycine (26 g.), m.p. 210 to 211° C (decomp.).

$[\alpha]_D^{20} + 5.6°$ (C=1, H$_2$O)

The salt (26 g.) obtained above was treated in a similar manner to Example 1 - (1) to give D-2-(4-hydroxyphenyl)glycine (8.4 g.), m.p. 213° to 215° C.

$[\alpha]_D^{20} - 108°$ (C=1, H$_2$O)

EXAMPLE 2

A mixture of DL-2-(4-hydroxyphenyl)glycine (20 g.), d-3-bromo-2-oxo-10-bronanesulfonic acid (39.2 g.) and methanol (50 ml.) was stirred for 30 minutes at 50° C and filtered. The filtrate was concentrated under reduced pressure. 50 ml. of isobutyl alcohol were added to the residue and the solution was evaporated again under reduced pressure. The oily residue was dissolved in isobutyl alcohol (150 ml.) and the solution was seeded with the authentic specimen of d-3-bromo-2-oxo-10-bornanesulfonic acid salt of L-2-(4-hydroxyphenyl)glycine and allowed to stand overnight at 0° C. The precipitates were collected by filtration, washed with isobutyl alcohol (50 ml.) and dried for 12 hours at room temperature under reduced pressure (5 mmHg) to give needles of the solvate. (25.6 g.) of d-3-bromo-2-oxo-10-bornanesulfonic acid salt of L-2-(4-hydroxyphenyl)glycine with isobutyl alcohol, m.p. 190° to 193° C (decomp).

A solution of the solvate (25.6 g.) and hot methanol (50 ml.) was evaporated under reduced pressure, and the oily residue was dissolved in isobutyl alcohol (80 g.). The solution was allowed to stand overnight at 0° C. The precipitating crystals were collected by filtration and dried for 24 hours at 70° C under reduced pressure (1 mmHg) to give the pure solvate (22 g.), m.p. 190° to 193° C (decomp.). The differential thermal analysis of this solvate gave the endothermic peaks at 125° to 143° C and 143° to 160° C.

$[\alpha]_D^{20} + 117°$ (C=1, H$_2$O)

This solvate (22 g.) was treated in a similar manner to Example 1 – (1) to give L-2-(4-hydroxyphenyl)glycine (6.4 g.), m.p. 214° to 215° C, (decomp.).

$[\alpha]_D^{20} + 108°$ (C=1, H$_2$O)

EXAMPLE 3

(1) A mixture of DL-2-(4-hydroxyphenyl)glycine (10 g.), d-3-bromo-2-oxo-10-bornanesulfonic acid (20 g.) and hot 99% ethanol (100 ml.) was filtered, and the filtrate was concentrated under reduced pressure to a total weight of 40 g. Chloroform (265 g.) was added to the solution, and the solution was seeded with the authentic specimen of d-3-bromo-2-oxo-10-bornanesulfonic acid salt of L-2-(4-hydroxyphenyl)glycine and allowed to stand for 2 hours at room temperature. The precipitating crystals were collected by filtration, washed with a mixture of ethanol and chloroform (5 : 1) and dried for 12 hours at room temperature under reduced pressure to give the solvate (16.1 g.) of d-3-bromo-2-oxo-10-bronanesulfonic acid salt of L-2-(4-hydroxyphenyl)glycine with chloroform. Recrystallization from a mixture of ethanol (20 g.) and chloroform (250 g.) in a similar manner to the above gave the pure solvate (15.1 g.), m.p. 190° to 197° C. The differential thermal analysis of this solvate gave the endothermic peak at 155° to 156° C.

$]\alpha]_D^{20} + 107°$ (C=1, H$_2$O)

This solvate (15.1 g.) was treated in a similar manner to Example 1 − (1) to give L-2-(4-hydroxyphenyl)glycine (3.8 g.), m.p. 213° to 214° C (decomp.)
$[\alpha]_C^{20}$ + 106° (C=1, H$_2$O)

(2) The filtrate and washings, which were obtained in the above by removing the crude solvate of d-3-bromo-2-oxo-10-bornanesulfonic acid salt of L-2-(4-hydroxyphenyl)glycine with chloroform, were evaporated under reduced pressure. The oily residue was dissolved in ethanol (20 g.). 350 g. of chloroform were added to the solution and the solution was seeded with the authentic specimen of d-3-bromo-2-oxo-10-bornanesulfonic acid salt of D-2-(4-hydroxyphenyl)glycine and allowed to stand overnight at room temperature. The precipitating crystals were collected by filtration, washed with a mixture of ethanol and chloroform (2 : 35) and dried to give d-3-bromo-2-oxo-10-bronanesulfonic acid salt of D-2-(4-hydroxyphenyl)-glycine (161.1 g.). Recrystallization from a mixture of ethanol (20 g.) and chloroform (250 g.) in a similar manner to the above gave the pure salt (13 g.), m.p. 209 to 210° C.

The salt was treated in a similar manner to Example 1-(1) to give D-2-(4-hydroxyphenyl)glycine (4.1 g.), m.p. 211° to 212° C.
$[\alpha]_D^{20}$ − 106° (C=1, H$_2$O)

what we claim is:
1. A process for the resolution of D-and L-2-(4-hydroxyphenyl)glycine which comprises treating DL-2-(4-hydroxyphenyl)glycine with d-3-bromo-2-oxo-10-bornanesulfonic acid to form a mixture of d-3-bromo-2-oxo-10-bornanesulfonic acid salts of D- and L-2-(4-hyroxyphenyl)glycine, treating the mixture with a solvent selected from the group consisting of a mixture of lower alkanol and chloroform or a mixture of lower alkanol and toluene to selectively precipitate a solvate of the d-3-bromo-2-oxo-10-bornanesulfonic acid salt of L-2-(4-hydroxyphenyl)glycine with chloroform or toluene.

2. The process according to claim 1 further comprising collecting said precipitate.

3. The process according to claim 2 further comprising obtained d-3-bromo-2-oxo-10-bornanesulfonic acid salt of D-2-(4-hydroxyphenyl) glycine from the mother liquor containing lower alkanol.

4. The process according to claim 3 wherein D-2-(4-hydroxyphenyl)glycine is isolated.

5. The process according to claim 1 wherein a mixture of chloroform and ethanol is used as said solvent.

6. The process according to claim 1 wherein a mixture of toluene and isopropyl alcohol is used as said solvent.

7. The process according to claim 4 wherein a mixture of chloroform and ethanol is used as said solvent.

8. The process according to claim 4 wherein a mixture of toluene and isopropyl alcohol is used as said solvent.

9. The process according to claim 1 wherein L-2-(4-hydroxyphenyl)glycine is isolated.

10. The process according to claim 9 wherein a mixture of chloroform and ethanol is used as said solvent.

11. The process according to claim 9 wherein a mixture of toluene and isopropyl alcohol is used as said solvent.

12. The process according to claim 3 wherein said D-2-(4-hyroxyphenyl)glycine is recovered from d-3-bromo-2-oxo-10-bornanesulfonic acid salt of D-2-(4-hydroxyphenyl)glycine by the method comprising:
 a. dissolving said salt in a polar solvent,
 b. treating said salt in said polar solvent with a base having a stronger basicity than DL-2-(4-hydroxyphenyl)glycine whereby a solution is formed, and
 c. adding acid to said solution to attain a pH value of about 5 whereby D-2-(4-hydroxyphenyl)glycine is precipitated.

13. The process according to claim 12 further comprising treating said precipitate to obtain substantially pure D-2-(4-hydroxyphenyl)glycine.

14. The process according to claim 1 wherein said L-2-(4-hydroxyphenyl)glycine is recovered from said solvate by the method comprising:
 a. dissolving said solvate in a polar solvent,
 b. treating said solvate in said polar solvent with a base having a stronger basicity than DL-2-(4-hydroxyphenyl)glycine whereby a solution is formed, and
 c. adding acid to said solution to attain a pH value of about 5 whereby L-2-(4-hydroxyphenyl)glycine is precipitated.

15. The process according to claim 14 further comprising treating said precipitate to obtain substantially pure L-2-(4-hydroxyphenyl)glycine.

16. A process for the resolution of D- and L-2-(4-hydroxyphenyl)glycine with comprises treating DL-2-(4-hydroxyphenyl)glycine with d-3-bromo-2-oxo-10-bornanesulfonic acid to form a mixture of d-3-bromo-2-oxo-10-bornanesulfonic acid salts of D- and L-2-(4-hydroxyphenyl) glycine, treating the mixture with an excess of isobutyl alcohol to selectively precipitate a solvate of the d-3-bromo-2-oxo-10-bornanesulfonic acid salt of L-2-(4-hydroxyphenyl) glycine with isobutyl alcohol.

17. The process according to claim 16 further comprising collecting said precipitate.

18. The process according to claim 17 further comprising obtaining d-3-2-oxo-10-bornanesulfonic acid salt of D-2-(4-hydroxyphenyl)glycine from the mother liquor containing isobutyl alcohol.

19. The process according to claim 18 wherein D-2-(4-hydroxyphenyl)glycine is isolated.

20. The process according to claim 17 wherein L-2-(4-hydroxyphenyl)glycine is isolated.

21. The process according to claim 18 wherein said D-2-(4-hydroxyphenyl)glycine is recovered from d-3-bromo-2-oxo-10-bornanesulfonic acid salt of D-2-(4-hydroxyphenyl)glycine by the method comprising:
 a. dissolving said salt in a polar solvent,
 b. treating said salt in said polar solvent with a base having a stronger basicity than DL-2-(4-hydroxyphenyl)glycine whereby a solution is formed, and
 c. adding acid to said solution to attain a pH value of about 5 whereby D-2-(4-hydroxyphenyl)glycine is precipitated.

22. The process according to claim 21 further comprising treating said precipitate to obtain substantially pure D-2-(4-hydroxyphenyl)glycine.

23. The process according to claim 12 wherein said L-2-(4-hydroxyphenyl)glycine is recovered from said solvate by the method comprising:
 a. dissolving said solvate in a polar solvent,
 b. treating said solvate in said polar solvent with a base having a stronger basicity than DL-2-(4-hydroxyphenyl)glycine whereby a solution is formed, and
 c. adding acid to said solution to attain a pH value of about 5 whereby L-2-(4-hydroxyphenyl)glycine is precipitated.

24. The process according to claim 23 further comprising treating said precipitate to obtain substantially pure L-2-(4-hydroxyphenyl)glycine.

* * * * *